(12) United States Patent
Hartley

(10) Patent No.: US 9,610,128 B2
(45) Date of Patent: *Apr. 4, 2017

(54) POUCH FOR MEDICAL INSTRUMENTS AND DEVICES

(71) Applicant: Westfield Medical Limited, Radstock (GB)

(72) Inventor: Paul Hartley, Bristol (GB)

(73) Assignee: Westfield Medical Limited, Radstock (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/988,812

(22) Filed: Jan. 6, 2016

(65) Prior Publication Data

US 2016/0128778 A1   May 12, 2016

Related U.S. Application Data

(63) Continuation of application No. 13/643,069, filed as application No. PCT/GB2011/000647 on Apr. 26, 2011, now Pat. No. 9,254,176.

(30) Foreign Application Priority Data

Apr. 23, 2010   (GB) .................................. 1006807.0

(51) Int. Cl.
  *A61B 19/02*   (2006.01)
  *A61B 50/39*   (2016.01)
  *A61B 50/36*   (2016.01)
  *A61B 50/30*   (2016.01)
  *A61B 50/00*   (2016.01)

(52) U.S. Cl.
  CPC .......... *A61B 19/0287* (2013.01); *A61B 50/30* (2016.02); *A61B 50/36* (2016.02); *A61B 50/39* (2016.02); *A61B 2050/002* (2016.02); *A61B 2050/005* (2016.02); *A61B 2050/3005* (2016.02); *A61B 2050/314* (2016.02); *A61B 2050/316* (2016.02); *A61B 2050/318* (2016.02)

(58) Field of Classification Search
  CPC . B65D 85/00; A61B 19/02; A61B 2019/0201; A61B 2019/0267; A61B 2019/027; A61B 2019/0287; A61B 50/20; A61B 50/30; A61B 50/37; A61B 50/36; A61B 2050/3008; A61B 2050/315; A61B 2050/314; A61F 17/00
  USPC ....... 206/570, 362, 370, 438, 363, 372, 204; 383/37, 38
  See application file for complete search history.

(56) References Cited

U.S. PATENT DOCUMENTS

| | | | | |
|---|---|---|---|---|
| 3,749,237 A | * | 7/1973 | Dorton | A61B 19/029 206/390 |
| 3,858,789 A | * | 1/1975 | Verbeke | B31B 19/86 383/7 |
| 4,194,622 A | * | 3/1980 | Lewis | A61B 19/026 206/363 |

(Continued)

*Primary Examiner* — Steven A. Reynolds
(74) *Attorney, Agent, or Firm* — Edwin D. Schindler

(57) ABSTRACT

A pouch is formed from one or more webs of material that provide at least one absorbent surface. The pouch further includes an integral flap, which may be folded over the opening, or entrance, of the pouch so as to maintain the contents of the pouch in place and to help retain moisture within the pouch. The interior of the pouch is defined, at least partially, by its absorbent faces.

6 Claims, 2 Drawing Sheets

(56) References Cited

U.S. PATENT DOCUMENTS

| | | | | |
|---|---|---|---|---|
| 4,234,086 A * | 11/1980 | Dorton | B65D 33/002 | 206/286 |
| 4,361,231 A * | 11/1982 | Patience | A61B 19/029 | 206/286 |
| 4,619,361 A * | 10/1986 | Thomas, Jr. | B65D 81/264 | 206/204 |
| 4,713,136 A * | 12/1987 | Li | | 156/229 |
| 4,742,908 A * | 5/1988 | Thomas, Jr. | B65D 81/264 | 206/204 |
| 4,785,940 A * | 11/1988 | Wilson | B65D 33/20 | 383/204 |
| 4,815,590 A * | 3/1989 | Peppiatt | B65D 81/264 | 206/204 |
| 4,861,632 A * | 8/1989 | Caggiano | B32B 7/02 | 206/204 |
| 4,887,715 A * | 12/1989 | Spahn | A61B 19/029 | 206/362 |
| 4,984,907 A * | 1/1991 | Power | B65D 81/264 | 206/204 |
| 5,222,600 A * | 6/1993 | Stoddard | A61B 19/0262 | 206/369 |
| 5,404,999 A * | 4/1995 | Bednar | A01K 1/0107 | 206/204 |
| 5,429,234 A * | 7/1995 | Bohannon | A61B 19/029 | 206/362 |
| 5,539,934 A * | 7/1996 | Ponder | A42B 3/285 | 2/413 |
| 5,658,077 A * | 8/1997 | Hoftman | A61B 19/029 | 206/362 |
| 5,885,262 A * | 3/1999 | Wheeler | A61B 19/0287 | 156/580.1 |
| 6,089,367 A * | 7/2000 | Anderson | B65D 81/264 | 206/204 |
| 6,298,983 B1 * | 10/2001 | Yeager | B31B 1/02 | 206/204 |
| 6,607,170 B1 * | 8/2003 | Hoftman | A61B 19/029 | 206/370 |
| 7,806,594 B2 * | 10/2010 | Trinko | B65D 33/001 | 206/554 |
| 8,371,448 B1 * | 2/2013 | Reaux | A61B 19/029 | 206/362 |
| 2002/0079238 A1 * | 6/2002 | Wilson, Jr. | B65D 81/264 | 206/204 |
| 2004/0178099 A1 * | 9/2004 | Natay-Curley | A61L 2/07 | 206/370 |
| 2010/0078351 A1 * | 4/2010 | Sherrill | A61F 13/551 | 206/570 |
| 2010/0187135 A1 * | 7/2010 | Broering | B65F 1/0006 | 206/204 |

* cited by examiner

POUCH FOR MEDICAL INSTRUMENTS AND DEVICES

CROSS-REFERENCE TO PRIOR APPLICATION

This is a continuation of application Ser. No. 13/643,069, filed Nov. 6, 2012, which represents the U.S. National Phase patent application of P.C.T. Application No. PCT/GB2011/000647, filed Apr. 26, 2011, now U.S. Pat. No. 9,254,176 B2.

FIELD OF THE INVENTION

This invention relates to pouches for holding medical instruments and medical devices such as implants. These articles may be loaded into the pouch either as separate items or within holding trays or baskets.

BACKGROUND TO THE INVENTION

Traditionally, the purpose of a medical pouch has been to provide a sterile barrier for instruments and devices up to the point of use. After use, the soiled articles are sent to a washing/disinfecting facility in bags or containers which allow protein to dry on the instruments, thereby rendering them difficult to clean.

STATEMENTS OF THE INVENTION

According to the present invention there is provided a pouch formed from one or more webs of material providing at least one absorbent surface, the pouch having an integral flap which may be folded over the entrance of the pouch so as to maintain the contents of the pouch in place and help to retain moisture within the pouch, and the interior of the pouch being defined at least partly by the or each absorbent surface. In use therefore, an item, such as a medical instrument will be located within the pouch along with the absorbent surface or surfaces.

A pouch in accordance with the present invention is intended to provide a moist environment for the bag contents at and beyond the point of use. Such an environment reduces the drying of protein and other debris on the instruments, thus facilitating easier cleaning prior to sterilisation.

To achieve and maintain a moist environment within the pouch, liquid is introduced into the pouch and is allowed to permeate the absorbent surfaces prior to use. The liquid may be a sterile liquid and/or it may contain one or more additives. The liquid is preferably an aqueous liquid.

Preferably, the pouch comprises first and second substantially rectangular webs of material, at least one of which has an absorbent surface on one side thereof, the webs being of the same length but of different width and being sealed together along respective three edges of each web so that the web of greater width extends beyond the free edge of the web of lesser width to provide a flap for folding over the web of lesser width and also for facilitating ease of entry of the instruments or trays into the pouch.

Alternatively, the pouch may comprise first and second substantially rectangular webs of material and a third web located between said first and second webs and having at least one absorbent surface, the first and second webs being of the same length but of different width and being sealed together along respective three edges of each web so that the web of greater width extends beyond the free edge of the web of lesser width to provide a flap for folding over the web of lesser width and also for facilitating ease of entry of the instruments or trays into the pouch.

Preferably, the pouch is formed by at least one web of absorbent material.

Preferably, the pouch is provided with at least one web of water imperious plastics film.

One or both of the flaps and the outer surface of the web of lesser width is provided with means for securing the flap to the outer surface of the web of lesser width. Preferably, such securing means is provided on the flap.

Preferably, the securing means is double sided tape.

The first and second webs may be provided by a single piece of folded over material or alternatively by separate pieces of material.

Preferably, the webs are additionally joined together at one or more positions along the length of the pouch to provide pockets for accommodating medical instruments.

For example, the webs may be joined together at two positions along the length of the pouch to provide three pockets.

The present invention also provides a method of storing a medical instrument or component in a moist environment, the method comprising locating the instrument or component within a pouch as claimed in any of the preceding claims, the or each absorbent surface being permeated with liquid.

The pouch may be provided in "wet" condition, that is to say, with the or each absorbent surface permeated with liquid. Alternatively, it may be in "dry" form with liquid supplied in a separate container, from which it is added to the pouch. As a further alternative, the pouch may be supplied dry and the user may make up a suitable liquid for addition to the pouch.

DETAILED DESCRIPTION OF THE INVENTION

The present invention will now be described, by way of examples only, with reference to the accompanying drawings.

Figure 1:
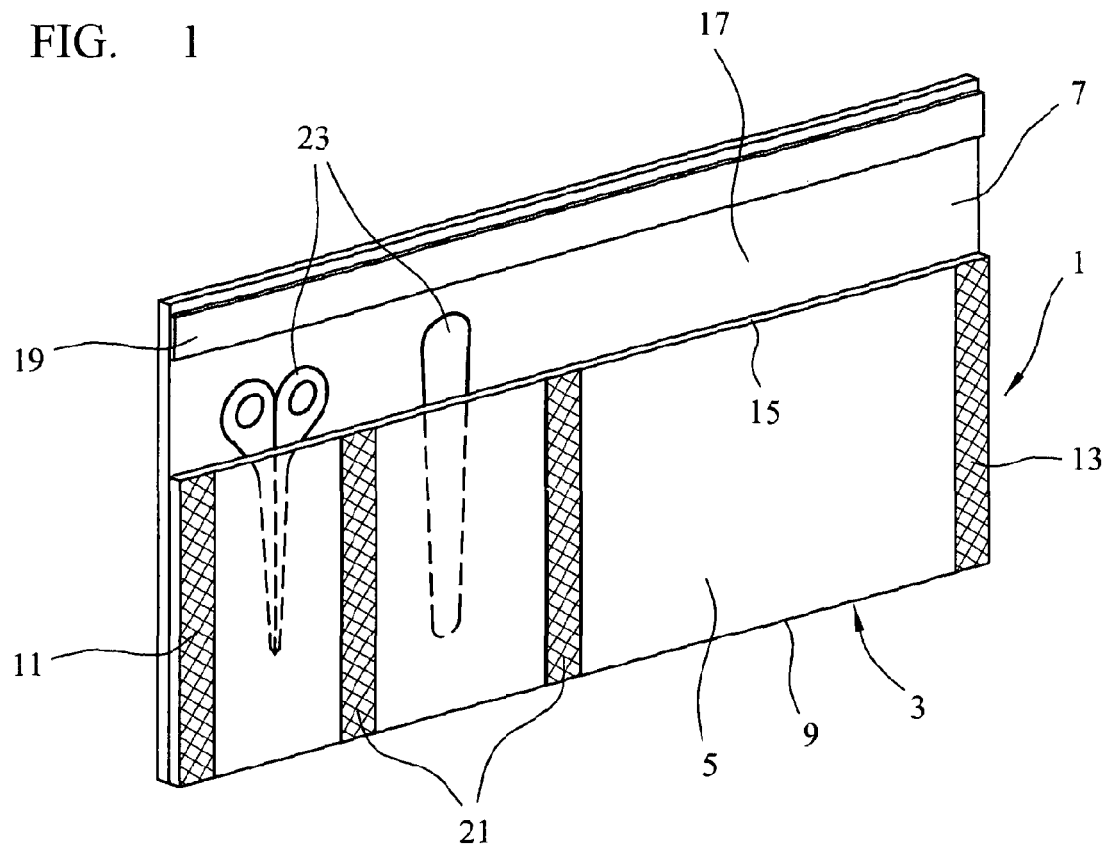
FIG. 1 is a perspective view of a medical pouch in accordance with the present invention.

Referring to FIG. 1 of the accompanying drawings, a medical pouch 1 is for use in holding surgical instruments in a moist environment both during and after use.

Pouch 1 includes a web of material 3 which may consist of two separate pieces of material 5, 7 or a single piece of material folded at 9. The surface or surfaces which provide the inner surfaces of the pouch are liquid absorbent.

As shown in the drawing, the webs 5 and 7 are rectangular and of the same length but of different width. They are connected together at 9 (or folded about 9) and also along edges 11 and 13. Because of the different widths, web 7 extends beyond the edge 15 of web 5 to form a flap 17 which extends from the open edge of the pouch.

Flap 17 may be provided with a strip of double sided tape 19 which extends along the length of the flap at a position close to its free edge.

Pouch 1 may be divided into sealed compartments by means of seals 21 which extend parallel to edges 11 and 13. As a result there are provided three compartments for holding instruments 23.

With instruments in place in the pouch, the release liner may be removed from tape 19 and the flap folded over to retain the instruments within the pouch, and also to help retain the moist atmosphere within the pouch. When access to the instruments is required, the flap can be easily detached from the body of the pouch.

The above described pouch allows instruments to be maintained in a moist environment both during and after use. Material, such as protein, adhering to the instruments may be kept moist thereby allowing for easy cleaning prior to sterilisation of the instruments.

Sterile liquid may be introduced into the pouch to achieve and maintain a moist environment.

It should be appreciated that the above described pouch can be modified in many ways within the scope of the present invention. For instance, the webs may be of equal length, tape to hold the flap down may be omitted and the pouch may be made of three (or more) webs.

Figure 2:
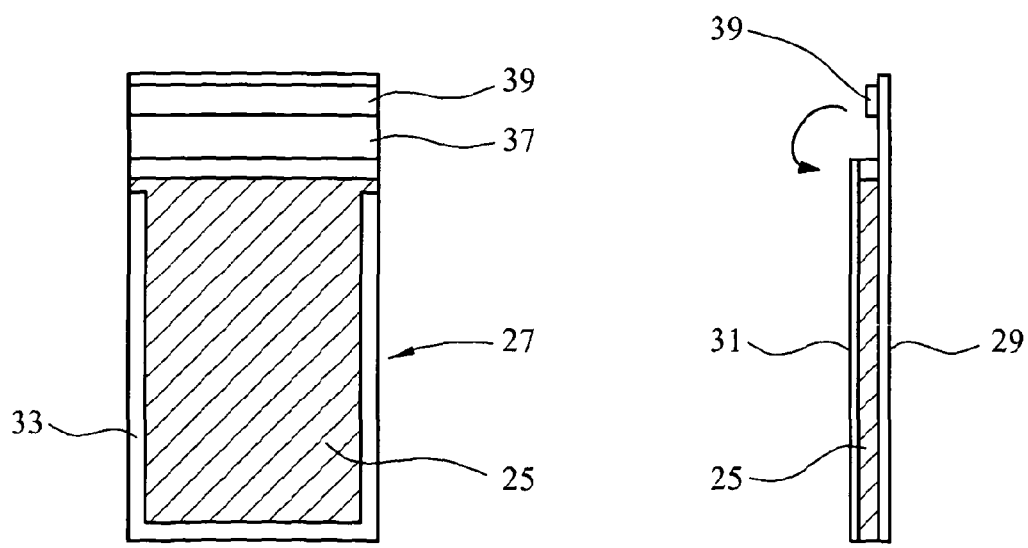
FIGS. 2 to 4 are, in each case, front and longitudinal sectional views of three further embodiments of the present invention.
Figure 3:
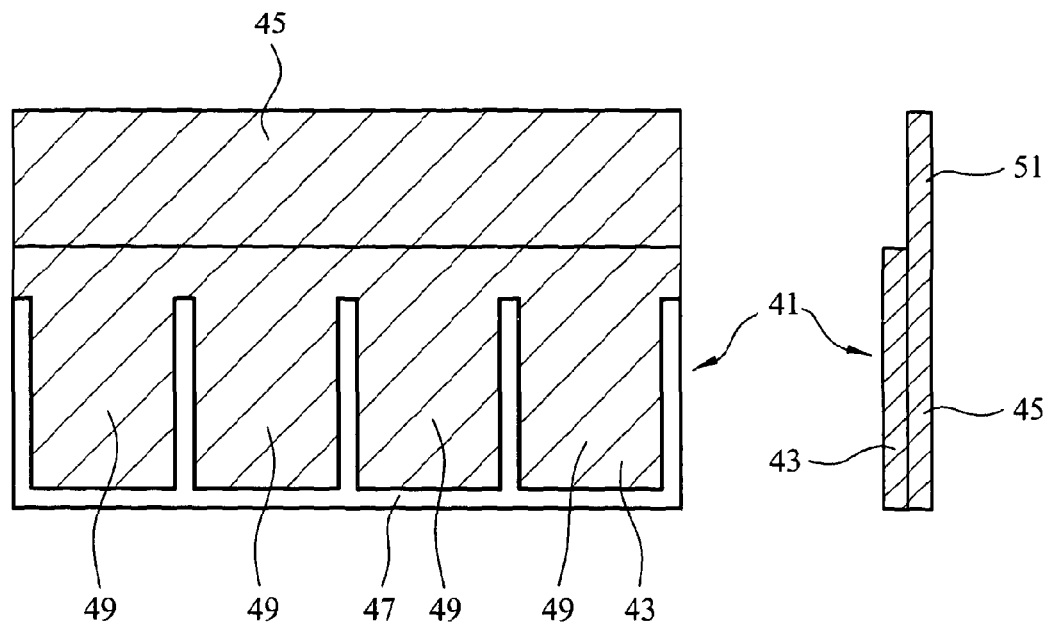
Figure 4:
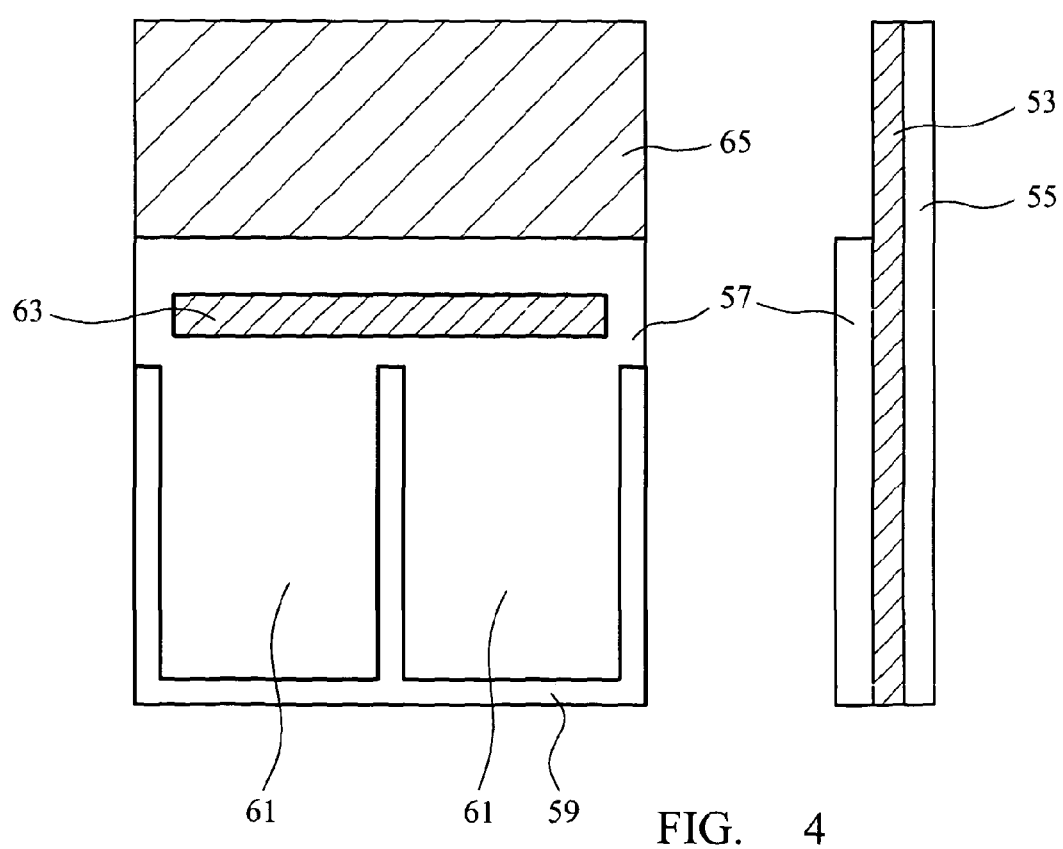

Various pouches, within the scope of the present invention, are illustrated in FIGS. 2 to 4. In each case, the pouch makes use of at least one web of absorbent material 25. This web may be, for instance, of 100% viscose material, made of viscose rayon and binder (73% viscose rayon fibre/27% binder). The material may be impregnated with an absorbency increasing agent. The material has low linting, that is to say, it has a low level of loose fibres and does not disintegrate easily as a result of instrument abrasion.

Referring to FIG. 2, a pouch 27 comprises a layer of absorbent material 25 having a backing of a transparent plastics film 29. A shorter layer of plastics film 31 is provided at the front of absorbent layer 25. The three layers are secured together by sealing about a substantial portion of the edges as indicated at 33. The absorbent layer 25 is shorter than both plastics film layers 29 and 31.

The plastics film 31 may be made of any suitable transparent, translucent or opaque material. Examples are a polyester/polypropylene or polyester/polyethylene film which might be a laminate, or a non-laminate. A film containing polypropylene might be used if the pouch and its contents are to be subjected to a steam sterilisation process. A film containing polyethylene might be used where the pouch and its contents are to be subjected to EB (electron beam radiation) or γ radiation.

The film 31 may or may not be provided with small holes to allow steam to escape from the pouch.

The flap 37, which is that portion of webs 29 extending above web 31, may be folded over the front of web 31 when the pouch is loaded with an instrument. Flap 37 is provided with a strip 39 of double sided adhesive tape.

Referring to FIG. 3 of the accompanying drawings, a pouch 41 is formed from two webs of absorbent material 43 and 45. The webs are connected together by means of seals indicated at 47. As a result, pockets are provided at 49 and these pockets may accommodate surgical instruments or associated components.

Rear web 45 extends beyond front web 43 and the flap 51 may be folded over the web when the instruments are contained within the pouch.

Referring to FIG. 4 of the accompanying drawings, a further embodiment of a pouch in accordance with the present invention has a layer of absorbent material 53 backed by a layer of transparent plastics film 55. Located at the front of web 53 is a further layer of transparent plastics film 57 and the three layers are sealed together as indicated by sealing 59. The result is that two pockets 61 are provided and these can accommodate instruments located between the plastics film 57 and absorbent layer 53.

Fixed to plastics film 57, at a position above the sealing areas 59 is a strip of double sided adhesive tape 63. Tape 63 is provided with a protective backing (on its front side) which may be peeled off. The flap 65, above the upper edge of layer 57 may then be folded over the front of layer 57 and secured to the adhesive layer 63 in order to maintain the instruments within the pockets 61 of the pouch 57.

It should be appreciated that pouches may be made in various combinations of absorbent and non-absorbent layers. A plastics film located on the front side of an absorbent layer provides visibility of the contents of the pockets and has some effect on water retention. If a plastic film is provided on both sides of the absorbent film, such as is the case in the FIG. 2 embodiment, then there is both visibility of instruments within the pouch and also a better water retention.

Tests have been carried out on various embodiments as follows:
1. An embodiment in which there is no plastics film (such as is shown in FIG. 3). In this case, a time interval of about two hours elapsed before the water had completely evaporated from the moistened pouch.
2. Film is provided on both sides of an absorbent layer (such as is shown in FIG. 4). In this case, a period of two days elapsed before the water has evaporated from the moistened pouch.
3. The pouch is similar to that of FIG. 4 except that the front plastics layer is perforated to allow for steam sterilisation. In this case a period of four hours elapsed before water evaporated from the moistened pouch.

The invention claimed is:
1. A medical pouch, comprising:
a first panel consisting of a single layer of absorbent material and a single layer of plastic film; and,
a second panel consisting of a single layer of plastic film;
wherein said first panel and said second panel are sealed together in a fixed relationship relative to one another for forming a pocket having an unsealed end for accommodating articles located between said first panel and said second panel,
said single layer of absorbent material of said first panel forming one interior side of said pocket for accommodating articles and said single layer of plastic film of said second panel forming one interior side of said pocket for accommodating articles, so that articles located in said medical pouch are located between said single layer of plastic film of said second panel and said single layer of absorbent material of said first panel,
said single layer of plastic film of said first panel and said single layer of absorbent material of said first panel being proximately sealed along an entirety of an outer perimeter of said medical pouch for maintaining a moist environment for the articles accommodated within said pocket of said medical pouch; and,
a flap foldable over an entrance of said medical pouch for maintaining the articles of said medical pouch in place and for retaining the moisture within said medical pouch, said flap being provided at the unsealed end of said pocket.

2. The medical pouch according to claim 1, wherein said single layer of absorbent material of said first panel, and said single layer of plastic film of said second panel are sealed together in a fixed relationship relative to one another for forming a plurality of pockets for accommodating a plurality of said articles.

3. The medical pouch according to claim 1, wherein said flap is integral with the unsealed end of said pocket.

4. The medical pouch according to claim 1, wherein said single layer of plastic film of said first panel and said single layer of plastic film of said second panel are each a substantially water imperious plastic film.

5. The medical pouch according to claim 1, wherein said flap includes means for securing said flap to an outer surface of said pouch.

6. The medical pouch according to claim 5, wherein said means for securing said flap to the outer surface of said pouch is double-sided tape.

* * * * *